United States Patent

Pohndorf et al.

[11] Patent Number: 5,358,517
[45] Date of Patent: Oct. 25, 1994

[54] ELECTRICAL MEDICAL LEAD WITH TEXTURED STYLET GUIDE

[75] Inventors: Peter J. Pohndorf, Stillwater; Richard L. Molacek, Maple Grove, both of Minn.

[73] Assignee: Medtronic, Inc., Minneapolis, Minn.

[21] Appl. No.: 4,389

[22] Filed: Jan. 14, 1993

[51] Int. Cl.⁵ .............................................. A61N 1/05
[52] U.S. Cl. .................................. 607/116; 607/119; 604/282
[58] Field of Search .............. 607/115, 116, 122, 123, 607/125, 126, 128, 130, 131, 119, 127; 604/164, 165, 282

[56] References Cited

U.S. PATENT DOCUMENTS

| | | | |
|---|---|---|---|
| 4,428,379 | 1/1984 | Robbins et al. | 128/662.05 |
| 4,431,006 | 2/1984 | Trimmer et al. | 128/662.05 |
| 4,955,862 | 9/1990 | Sepetka | 604/164 |
| 4,967,755 | 11/1990 | Pohndorf | 607/122 X |

FOREIGN PATENT DOCUMENTS 9117782  11/1991  World Int. Prop. O. .......... 604/282

Primary Examiner—Lee S. Cohen
Assistant Examiner—Jeffrey R. Jastrzab
Attorney, Agent, or Firm—Reed A. Duthler; Harold R. Patton

[57] ABSTRACT

An implantable lead having a plastic stylet guide therein. A substantially cylindrical channel is provided in a flexible lead body made of silicone rubber, polyurethane, or the like. The cylindrical channel defines a lumen containing a stylet guide into which a stylet can be inserted during an implantation procedure. Texture on the inner wall of the stylet guide minimizes friction between the stylet and the stylet guide, facilitating easy insertion and removal of the stylet. One or more electrical conductors may also be provided.

4 Claims, 1 Drawing Sheet

ELECTRICAL MEDICAL LEAD WITH TEXTURED STYLET GUIDE

BACKGROUND OF THE INVENTION

This invention relates to the field of electromedical devices, and more particularly relates to leads for use in conjunction with medical devices.

A wide variety of implantable medical devices such as cardiac pacemakers, cardioverters, defibrillators, neneural stimulators, and the like, have been known and commercially available for many years. Often, such devices are used in conjunction with one or more leads, which serve to conduct electrical stimulating pulses from the device to a desired location in the body, for example, the atrium or ventricle of a patient's heart. A lead may also serve to conduct electrical signals, such as a patient's electrical cardiac signals, to the implanted device.

In the case of cardiac pacing leads, the lead is introduced into the patient through a small incision at or near the implant site. The distal end of the lead is first introduced into the patient's vein. Then, the implanting physician directs the distal end of the lead through the vein and into the heart. Once the lead is positioned, the proximal end is connected to the implantable pacemaker. A somewhat larger incision is then made at the implant site, allowing, the pacemaker to be inserted under the skin.

In order to facilitate the introduction of a lead into the patient, a stylet can be employed. A stylet is a relatively stiff wire-like element that may be used during the implantation procedure to give the lead increased rigidity. In order to use a stylet the lead must be designed to permit insertion of the stylet into a cylindrical bore, or lumen. The lumen may be defined by a coiled lead conductor or by a separate plastic tube. Both alternatives are illustrated in U.S. Pat. No. 3,348,548, issued to Chardack. Alternatively, a tubular plastic stylet guide may be located in the lumen of a coiled conductor, as illustrated in U.S. Pat. No. 4,944,088, issued to Doan et al.

Often, a physician will impart a curve to the stylet, for example at the stylet's distal end, so that after insertion of the stylet into the lead, the curvature of the stylet is imparted to the lead itself. The curvature of the stylet, and hence of the lead surrounding the stylet, can greatly facilitate the navigation of the lead through the venous system and to its desired location within the heart.

SUMMARY OF THE INVENTION

The present invention comprises an implantable lead provided with an internal stylet guide for facilitating the easy insertion and passage of a stylet. The present invention accomplishes this by means of a tubular stylet guide which exerts minimal frictional resistance on a stylet being inserted therein. Reduced friction is accomplished by means of internal ribbing or texturing, which reduces the points of contact between the stylet and the stylet guide. This aspect of the invention is valuable whether the stylet guide is mounted within a coiled conductor or is mounted within the lead body, separate from the lead conductors.

In the illustrated embodiment a lead having non-coiled conductors is illustrated, in which the stylet guide is mounted within the plastic lead body, separate from the conductors. The stylet guide is also provided with texturing or ribbing on its outer surface which in this context assists in maintaining the stylet guide fixedly mounted within the lead body. In this embodiment, the stylet guide assists in preventing undue bending of the lead and possible fatigue of the internal conductive elements and also assists in resisting crushing of the lead body.

BRIEF DESCRIPTION OF THE DRAWING

The foregoing and other aspects of the present invention will be best appreciated with reference to the detailed description of a specific embodiment of the invention, which follows, when read in conjunction with the accompanying drawings, wherein.

DETAILED DESCRIPTION OF THE INVENTION

Figure 1:
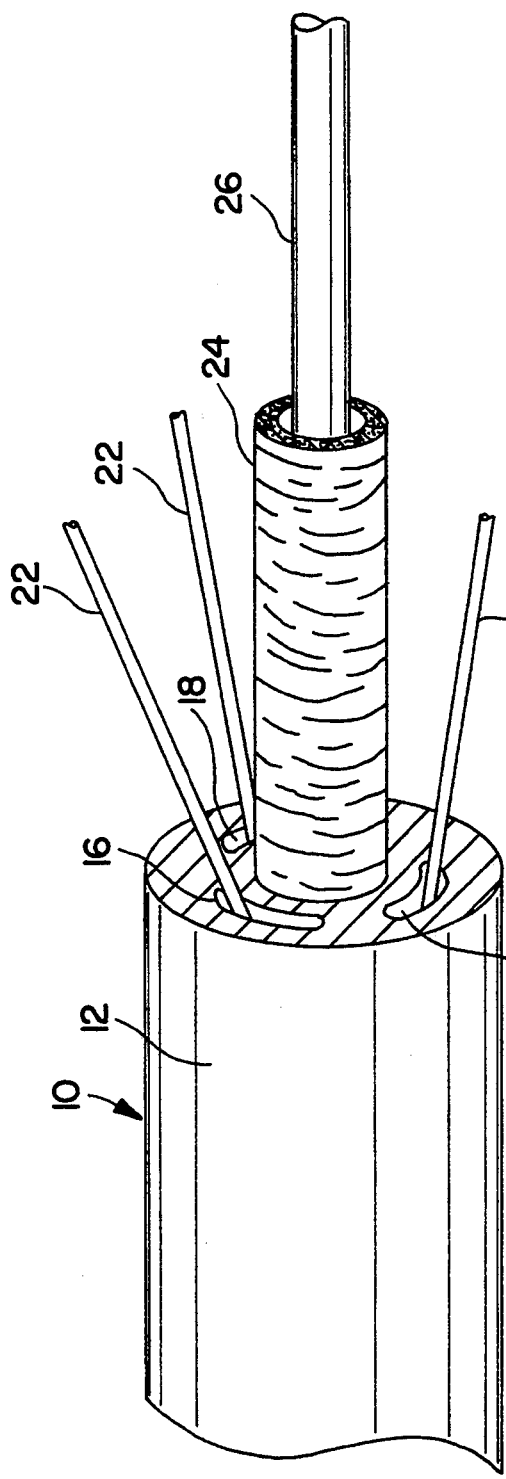
FIG. 1 is a perspective, cut-away view of a lead body in accordance with one embodiment of the invention.

FIG. 1, is a cut-away view of one end of a lead body 10 in accordance with one embodiment of the present invention. In the presently preferred and disclosed embodiment, lead body 10 comprises an outer resilient tubular member 12 having a plurality of intimal channels 14, 16, 18, and 20. As shown in FIG. 1, channel 20 is substantially centrally disposed along the longitudinal axis of tubular member 12, and is substantially cylindrical in form. In the illustrated embodiment of the invention, tubular member 12 is made of silicone rubber or polyurethane, although it is contemplated that other resilient, biocompatible materials may be equally suitable for the purposes of practicing the present invention.

In FIG. 1, channels 14, 16, 18 are each shown having a non-coiled conductive element 22 therein. Conductive elements 22 function as the lead conductors for conveying electrical signals between a remote site such as a sensor or electrode at one end of lead body 10 and an implanted device (not shown) at the other end of lead body 12. The lead conductors may be formed of twisted strands of wire made from MP35N alloy or other conductive, biocompatible metal. For example, the conductors may comprises seven strands of MP35N alloy, each with a diameter of 0.0005 to 0.030 inches, with six strands wound around a central strand at a pitch of 0.30 to 0.60 inches. The bundled strands may be left straight as illustrated or may be bent to follow a gentle serpentine or sigmoidal path. However, other conductor configurations may also be employed, including traditional coiled conductors in circular lumens.

It is contemplated by the inventors that channels 14, 16, and 18 may not all have conductive elements therein, but instead may serve as a passage-ways for communicating fluids and/or pressure gradients between the two ends of lead body 10. Channel 20 has a substantially cylindrical stylet guide 24 inserted therein. In the presently preferred embodiment of the invention, stylet guide 24 is an extruded plastic element having textured inner and outer surfaces. One material that is believed to be particularly suitable for the purposes of practicing the present invention is Kynar ® plastic, a product of Pennwalt Corporation, Philadelphia, Pa.

Figure 2:
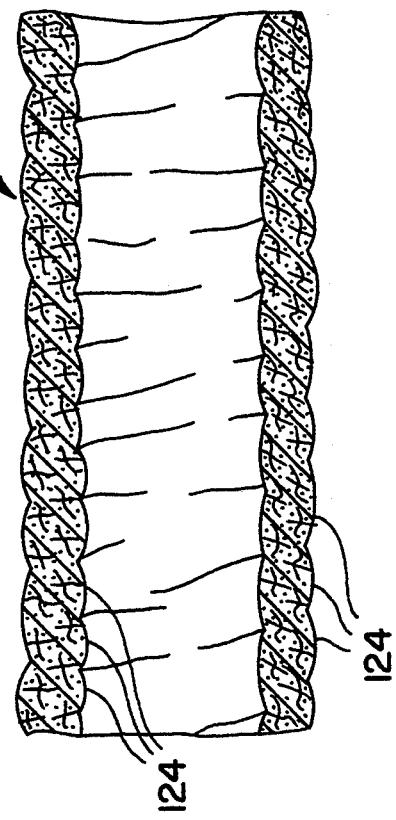
FIG. 2 is a sectional view through a stylet guide tube according to the present invention.

Kynar ® plastic tubing, as normally extruded, has smooth inner and outer walls. Normally, a smooth finish is accomplished by assuring that the tip of the extrusion die has temperatures 50–100 degrees F. higher than the die body. However, if the die tip temperature is not elevated, a surface roughness as illustrated in FIG. 2 will result. While normally undesirable, this surface roughness has a benefit when the tubing is used as a stylet guide. In FIG. 2 it can be seen that the extrusion process has produced irregular ridges or ribs 124 along both the inner and outer surfaces of the tube.

The textured inner surface of tube 24 allows a stylet, designated as 26 in FIG. 1, to be easily inserted and removed from lead body 10, as the ribs or ridges therein reduce the points of contact between the stylet and the guide tube 24. The ribbing or ridging on the exterior of the tube 24 assists in maintaining the tube stably in place within lead body 10. Adhesive may be also be used and the ridging is also of benefit in this case by enhancing the stability of the bond. The semi-rigidity of tube 24 resists crushing of lead body 10 and allows stylet 26 to move freely even when pressure is exerted against the outer wall of sleeve body 10. In addition, tube 24 resists the extreme bending and kinking of lead body 10 that can lead to fatigue and failure of internal conductive elements 22 and/or the partial or complete constriction of channels 14, 16, and 18.

Although a particular embodiment of the invention has been described here in some detail, this has been done for the purposes of illustration only, and is not to be taken as defining the scope of the present invention. For example, as discussed above, the textured stylet guide tube may be employed in leads having coiled conductors, and may in such cases be mounted within or outside of the coiled conductors. In addition, while the disclosed embodiment takes the form of a pacing lead, the invention may also be practiced in the form of a nerve or muscle stimulation lead or in any of a number of therapeutic and diagnostic catheters adapted for use with removable stylets. Therefore, the embodiment disclosed above should be considered exemplary, rather than limiting, with regard to the claims that follow.

What is claimed is:

1. An implantable lead, comprising:
   an elongated lead body having a substantially cylindrical, longitudinal axial bore;
   an elongated electrical conductor disposed in said lead body;
   an elongated, substantially cylindrical, hollow tubular member, formed of a plastic, disposed in said longitudinal axial bore, said hollow tubular member having a longitudinal axis and extruded to define an inner wall defining a lumen for receiving a stylet therein and having ridges formed therein generally perpendicular to said longitudinal axis of said tubular member, said ridges comprising means for contacting a said stylet received in said lumen.

2. An implantable lead in accordance with claim 1, wherein said elongated lead body is made of silicone rubber, 3. An implantable lead in accordance with claim 1, wherein said elongated lead body is made of polyurethane.

4. An implantable lead in accordance with claim 1 wherein said electrical conductor comprises a non-coiled conductor.

\* \* \* \* \*